United States Patent [19]

Someya et al.

[11] Patent Number: 4,753,671

[45] Date of Patent: Jun. 28, 1988

[54] 1,2,4-OXADIAZOLE DERIVATIVES, AND SELECTIVE HERBICIDAL COMPOSITIONS CONTAINING THEM

[75] Inventors: Shinzo Someya, Tokorozawa; Seigo Koura, Tokyo; Mikio Ito, Tokuyama; Akira Nakanishi, Yokohama; Kazuaki Tsukuda, Shin-nanyo; Yuji Nonaka, Tokuyama, all of Japan

[73] Assignee: Toyo Soda Mfg. Co., Tokyo, Japan

[21] Appl. No.: 49,055

[22] Filed: May 12, 1987

[30] Foreign Application Priority Data

May 16, 1986 [JP] Japan ................. 61-111930

[51] Int. Cl.$^4$ ................. C07D 413/12; A01N 43/82
[52] U.S. Cl. ................. 71/92; 546/277; 548/131
[58] Field of Search ............. 546/277; 548/131; 71/92

[56] References Cited

U.S. PATENT DOCUMENTS

| | | | |
|---|---|---|---|
| 3,954,442 | 5/1976 | Becker et al. | 71/108 |
| 4,238,626 | 12/1980 | Nahm et al. | 560/17 |
| 4,391,995 | 7/1983 | Nahm et al. | 560/62 |

FOREIGN PATENT DOCUMENTS

| | | |
|---|---|---|
| 2184906 | 3/1973 | France . |
| 175177 | 10/1982 | Japan . |
| 1599121 | 3/1978 | United Kingdom . |
| 2015995 | 9/1979 | United Kingdom . |
| 1599126 | 9/1981 | United Kingdom . |

OTHER PUBLICATIONS

Science, vol. 103, No. 2677, 19 Apr. 1946, pp. 472-473, Van Overbeek et al., "Use of 2,4-Dichlorophenoxyacetic Acid as a Selective Herbicide in the Tropics".
Chemical Abstracts, vol. 98, No. 23, 6 Jun. 1983, p. 657, Abstract No. 198238y.
Becker et al., CA 99:105236d.
Roechling et al., CA 81-49647c.

Primary Examiner—Jane T. Fan
Attorney, Agent, or Firm—Nixon & Vanderhye

[57] ABSTRACT

1,2,4-oxadiazole derivatives having selective herbicidal action in controlling broad leaf weeds and cyperaceous weeds without causing phytotoxicity to geraminous crop plants having the formula:

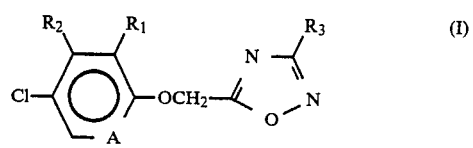

wherein A is a methine group or a nitrogen atom; $R_1$ is a chlorine atom or a methyl group; when A is a methine group, $R_2$ is a hydrogen atom if $R_1$ is a methyl group, and a hydrogen atom or a methyl group if $R_1$ is a chlorine atom, and when A is a nitrogen atom, $R_2$ is a hydrogen atom; $R_3$ is a hydrogen atom, an alkyl group having from 1 to 11 carbon atoms, a benzyl group unsubstituted or substituted by chlorine or methoxy; a phenoxymethyl group unsubstituted or substituted by chlorine or methyl, or a lower alkoxyalkyl group.

5 Claims, No Drawings

1,2,4-OXADIAZOLE DERIVATIVES, AND SELECTIVE HERBICIDAL COMPOSITIONS CONTAINING THEM

The present invention relates to novel 1,2,4-oxadiazole derivatives, a process for their production and selective herbicidal compositions containing them as active ingredients.

Phenoxy type herbicides such as 2,4-D, MCPA and MCPB have been commonly employed to control paddy field weeds other than gramineous weeds. However, they often bring about phytotoxicity to paddy rice plants depending upon the timing for the application or the soil or weather conditions. On the other hand, when the phenoxy type herbicides are used for foliage treatment for the crop plants in an upland field, an extremely high selectivity is required, since they will be in contact with crop plants. Depending upon the types and amounts of the weeds and crop plants, the timing of the application or the weather conditions, it may happen that the crop plants receive a serious damage.

Under the circumstances, it has been strongly desired to develop a herbicide which is capable of certainly controlling annual and perennial broad leaf weeds and cyperaceous weeds in paddy fields and yet bringing about no phytotoxicity to rice plants even under any one of the above-mentioned conditions. Likewise, it has been desired to develop a herbicide for foliage treatment, which is capable of killing broad leaf weeds without adversely affecting gramineous crop plants such as upland rice (*Oryza sativa*), corn (*Zea Mays*), wheats, barleys, sugar cane (*Saccharum officinarum*) or zoysia grasses.

It is an object of the present invention to provide a herbicide which can industrially be produced and which is capable of controlling broad leaf weeds and cyperaceous weeds without bringing about phytotoxicity to rice plants by either soil or foliage treatment during a wide range from the initial stage to the last stage after the transplantation of paddy rice plants, and which is also capable of controlling a wide range of broad leaf weeds without bringing about phytotoxicity to gramineous crop plants with a high selectivity when used for foliage treatment in an upland field.

The present invention provides a 1,2,4-oxadiazole derivative having the formula:

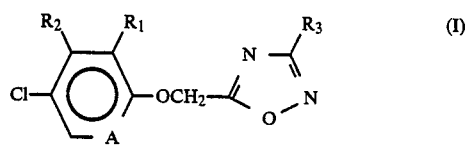

wherein A is a methine group or a nitrogen atom; $R_1$ is a chlorine atom or a methyl group; when A is a methine group, $R_2$ is a hydrogen atom if $R_1$ is a methyl group, and a hydrogen atom or a methyl group if $R_1$ is a chlorine atom, and when A is a nitrogen atom, $R_2$ is a hydrogen atom; $R_3$ is a hydrogen atom, an alkyl group having from 1 to 11 carbon atoms, a benzyl group unsubstituted or substituted by chlorine or methoxy; a phenoxymethyl group unsubstituted or substituted by chlorine or methyl, or a lower alkoxyalkyl group (hereinafter referred to as the compound of the present invention).

The compound of the formula I of the present invention can readily be prepared by a process which comprises reacting an aromatic compound of the formula:

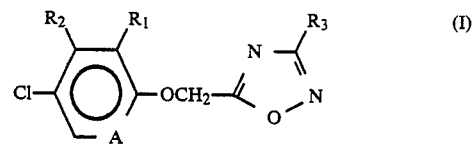

wherein A, $R_1$ and $R_2$ are as defined above, and X is a hydroxyl group when A is a methine group, and a halogen atom when A is a nitrogen atom, with a 5-methyl-1,2,4-oxazole derivative of the formula:

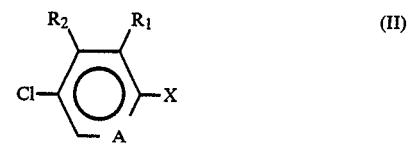

wherein $R_3$ is as defined above, and Y is a halogen atom when A is a methine group, and a hydroxyl group when A is a nitrogen atom.

The present invention also provides a selective herbicidal composition comprising a herbicidally effective amount of a 1,2,4-oxadiazole derivative of the formula I and an agricultural adjuvant.

Further, the present invention provides a method for killing weeds, which comprises applying a herbicidally effective amount of a 1,2,4-oxadiazole derivative of the formula I to a locus to be protected.

Now, the present invention will be described in further detail with reference to the preferred embodiments.

The compound of the formula I of the present invention can be prepared by various methods. The representative processes may be represented by the following reaction formulas.

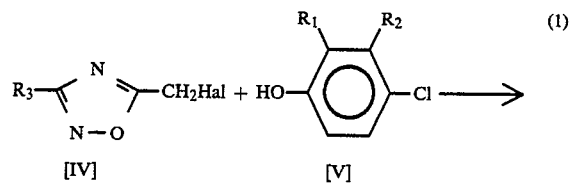

Compound of the present invention + H.Hal

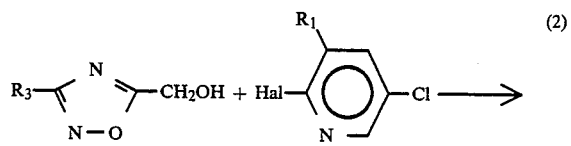

Compound of the present invention + H.Hal

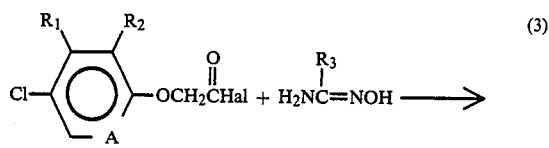

Compound of the present invention + H₂O + H.Hal

In the above formulas, A, $R_1$, $R_2$, $R_3$ and Hal are as defined above.

Among the above processes, the one represented by the reaction formula (1) will be described in further detail.

In the formula (1), a 5-halogenomethyl-1,2,4-oxadiazole derivative and a substituted phenol derivative are reacted in an organic solvent, preferably in the presence of a dehydrohalogenating agent, whereby the compound of the present invention is obtainable.

The reaction is conducted by using from 1 to 2 mols, preferably from 1.1 to 1.3 mols of the compound of the formula IV relative to the compound of the formula V, and the reaction proceeds under cooling with ice or at a temperature upto the refluxing temperature of the solvent. The reaction is conducted for a period of from a few minutes to 48 hours.

As the solvent, an alcohol such as methanol, ethanol or isopropanol, a ketone such as acetone or methyl ethyl ketone, an aromatic hydrocarbon such as toluene or xylene, an ether such as diethyl ether, tetrahydrofuran or dioxane, a halogenated hydrocarbon such as carbon tetrachloride or chloroform, or an organic solvent such as acetonitrile, ethyl acetate, dimethylformamide or dimethylsulfoxide, may be employed.

As the dehydrohalogenating agent, pyridine, triethylamine, potassium hydroxide, potassium carbonate, sodium ethylate or sodium hydride may, for example, be employed. The reaction can be conducted in good yield by using the dehydrohalogenating agent in an amount of from 1 to 3 equivalent to the compound of the formula V.

After the completion of the reaction, the reaction mixture is treated in accordance with a usual method such as recrystallization, distillation or column chromatography to isolate the compound of the present invention. Typical examples of the compounds thus obtained are shown in Table 1 together with their physical properties. However, it should be understood that the compound of the present invention is not limited to such typical examples.

TABLE 1

| Compound No. | $R_1$ | $R_2$ | $R_3$ | A | Physical properties | NMR ($\delta$ = ppm, CDCl$_3$) | Element analysis (%) Measured value (Calculated value) | | |
|---|---|---|---|---|---|---|---|---|---|
| | | | | | | | C | H | N |
| 1 | Cl | H | CH$_3$ | CH | mp 64–65° C. | 4.06(3H, s) 5.26(2H, s) 6.82–7.35(3H, m) | 46.19 (46.35) | 2.93 (3.11) | 10.84 (10.81) |
| 2 | Cl | H | H | CH | mp 63.5–64° C. | 5.33(2H, s) 6.86–7.40(3H, m) 8.45(1H, s) | 44.41 (44.11) | 2.59 (2.46) | 11.36 (11.43) |
| 3 | Cl | H | CH$_2$—C$_6$H$_5$ | CH | $n_D^{25}$ 1.5636 | 4.05(2H, s) 5.21(2H, s) 6.76–7.30(8H, m) | 57.38 (57.33) | 3.50 (3.60) | 8.41 (8.35) |
| 4 | Cl | H | C$_2$H$_5$ | CH | $n_D^{25}$ 1.5420 | 1.30(3H, t) 2.78(2H, q) 5.31(2H, s) 6.90–7.38(3H, m) | 48.43 (48.37) | 3.59 (3.69) | 10.60 (10.25) |
| 5 | Cl | H | CH$_3$ | N | $n_D^{25}$ 1.5484 | 2.41(3H, s) 5.64(2H, s) 7.68(1H, d) 7.96(1H, d) | 41.31 (41.56) | 2.86 (2.71) | 16.04 (16.15) |
| 6 | Cl | H | CH$_2$O—C$_6$H$_5$ | CH | mp 69–70° C. | 5.08(2H, s) 5.20(2H, s) 6.70–7.30(8H, m) | 55.08 (54.72) | 3.38 (3.44) | 8.32 (7.97) |
| 7 | Cl | H | (CH$_2$)$_4$CH$_3$ | CH | $n_D^{25}$ 1.5304 | 0.88(3H, t) 1.50(6H, mc) 2.75(2H, t) 5.32(2H, s) 6.85–7.38(3H, m) | 53.67 (53.34) | 5.07 (5.11) | 8.75 (8.88) |
| 8 | Cl | H | (CH$_2$)$_7$CH$_3$ | CH | $n_D^{25}$ 1.5215 | 0.85(3H, t) 1.50(12H, mc) 2.73(2H, t) 5.30(2H, s) 6.85–7.36(3H, m) | 56.78 (57.15) | 6.31 (6.20) | 8.20 (7.84) |
| 9 | Cl | H | CH$_2$—C$_6$H$_4$—OCH$_3$ | CH | $n_D^{25}$ 1.5770 | 3.72(3H, t) 4.03(2H, s) 5.15(2H, s) 6.72–7.30(7H, m) | 55.89 (55.90) | 3.99 (3.86) | 8.05 (7.67) |

TABLE 1-continued

Structure: R2, R1 on benzene ring with Cl and A substituents; -OCH2- linked to oxadiazole bearing R3

| Compound No. | R1 | R2 | R3 | A | Physical properties | NMR (δ = ppm, CDCl3) | C | H | N |
|---|---|---|---|---|---|---|---|---|---|
| | | | | | | | \multicolumn{3}{c}{Element analysis (%) Measured value (Calculated value)} | | |
| 10 | Cl | H | CH2-C6H4-OCH3 (para) | CH | n_D^25 1.5762 | 3.72(3H, s) 3.95(2H, s) 5.17(2H, s) 6.68–7.32(7H, m) | 56.02 (55.90) | 3.97 (3.86) | 7.47 (7.67) |
| 11 | Cl | H | CH2-C6H4-OCH3 (meta) | CH | n_D^25 1.5836 | 3.36(3H, s) 3.91(2H, s) 5.10(2H, s) 6.63–7.25(7H, m) | 55.80 (55.90) | 4.03 (3.86) | 7.39 (7.67) |
| 12 | Cl | H | CH2-C6H4-Cl (ortho) | CH | mp 73–73.5° C. | 4.23(2H, s) 5.27(2H, s) 6.78–7.32(7H, m) | 51.81 (51.99) | 2.90 (2.99) | 7.75 (7.57) |
| 13 | Cl | H | CH2-C6H4-Cl (meta) | CH | n_D^25 1.5870 | 4.00(2H, s) 5.20(2H, s) 6.76–7.27(7H, m) | 51.59 (51.99) | 2.88 (2.99) | 7.52 (7.57) |
| 14 | Cl | H | CH2-C6H4-Cl (para) | CH | n_D^25 1.5904 | 4.02(2H, s) 5.21(2H, s) 6.77–7.33(7H, m) | 52.00 (51.99) | 3.01 (2.99) | 7.64 (7.57) |
| 15 | Cl | H | CH2OCH3 | CH | mp 54.5–55.5° C. | 3.40(3H, s) 4.55(2H, s) 5.30(2H, s) 6.80–7.62(3H, m) | 45.32 (45.69) | 3.28 (3.48) | 10.03 (9.68) |
| 16 | Cl | H | CH2O-C6H4-CH3 (para) | CH | mp 82.5–84° C. | 2.20(3H, s) 5.10(2H, s) 5.25(2H, s) 6.71–7.30(7H, m) | 55.91 (55.90) | 4.03 (3.86) | 7.61 (7.67) |
| 17 | Cl | H | CH2CH2OCH3 | CH | mp 58–59° C. | 2.93(2H, t) 3.28(3H, s) 3.68(2H, t) 5.23(2H, s) 6.73–7.30(3H, m) | 47.84 (47.54) | 4.03 (3.98) | 9.49 (9.24) |
| 18 | Cl | H | CH2CH2OC2H5 | CH | n_D^25 1.5312 | 1.12(3H, t) 2.96(2H, t) 3.40(2H, q) 3.76(2H, t) 5.30(2H, s) 6.80–7.33(3H, m) | 49.61 (49.23) | 4.31 (4.44) | 8.85 (8.83) |
| 19 | Cl | H | CH2O-C6H4-Cl (meta) | CH | mp 41–42° C. | 5.13(2H, s) 5.28(2H, s) 6.72–7.32(7H, m) | 49.79 (49.83) | 2.86 (2.87) | 6.99 (7.26) |

TABLE 1-continued

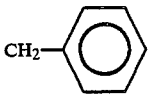

| Compound No. | R₁ | R₂ | R₃ | A | Physical properties | NMR (δ = ppm, CDCl₃) | Element analysis (%) Measured value (Calculated value) C | H | N |
|---|---|---|---|---|---|---|---|---|---|
| 20 | Cl | CH₃ | 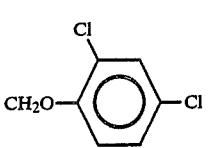 | CH | mp 58.5–60° C. | 2.30(3H, s) 3.97(2H, s) 5.08(2H, s) 6.47(1H, d) 7.02(1H, d) 7.16(5H, s) | 58.20 (58.47) | 4.10 (4.04) | 8.30 (8.02) |
| 21 | Cl | CH₃ | CH₃ | CH | mp 53.5–54° C. | 2.33(3H, s) 2.38(3H, s) 5.20(2H, s) 6.71(1H, d) 7.10(1H, d) | 48.48 (48.37) | 3.69 (3.69) | 10.20 (10.25) |
| 22 | Cl | H | 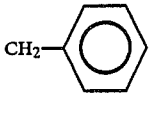 | CH | mp 121.5–122° C. | 5.20(2H, s) 5.34(2H, s) 6.87–7.28(6H, m) | 45.66 (45.74) | 2.19 (2.39) | 6.72 (6.66) |
| 23 | Cl | H | 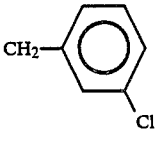 | N | mp 73–74° C. | 4.0(2H, s) 5.50(2H, s) 7.2–7.65(5H, m) 7.85(1H, d) 8.15(1H, d) | 53.40 (53.29) | 3.12 (3.29) | 12.69 (12.49) |
| 24 | Cl | H | C₂H₅ | N | $n_D^{25}$ 1.5486 | 1.45(3H, t) 2.73(2H, q) 5.60(2H, s) 7.65(1H, d) 7.90(1H, d) | 43.68 (43.81) | 3.47 (3.30) | 15.66 (15.32) |
| 25 | Cl | H | 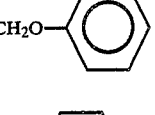 | N | $n_D^{25}$ 1.5904 | 4.0(2H, s) 5.55(2H, q) 7.15–7.68(4H, m) 7.86(1H, d) 8.17(1H, d) | 48.70 (48.61) | 2.77 (2.71) | 11.38 (11.33) |
| 26 | Cl | H | 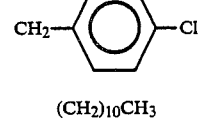 | N | mp 79.5–81° C. | 5.25(2H, s) 5.71(2H, s) 6.98–7.76(5H, m) 7.96(1H, d) 8.28(1H, d) | 51.27 (51.15) | 3.00 (3.14) | 12.07 (11.93) |
| 27 | Cl | H | 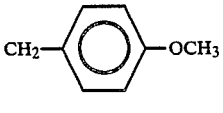 | N | mp 80–83° C. | 3.96(2H, s) 5.50(2H, s) 7.15–7.61(4H, m) 7.81(1H, d) 8.13(1H, d) | 48.77 (48.61) | 2.73 (2.71) | 11.54 (11.33) |
| 28 | Cl | H | (CH₂)₁₀CH₃ | CH | $n_D^{25}$ 1.5112 | 0.83(3H, t) 1.50(18H, mc) 2.70(2H, t) 5.27(2H, s) 6.82–7.30(3H, m) | 60.18 (60.15) | 7.21 (7.06) | 6.98 (7.01) |
| 29 | CH₃ | H | 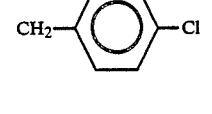 | CH | $n_D^{25}$ 1.5719 | 2.10(3H, s) 3.68(3H, s) 3.93(2H, s) 5.08(2H, s) 6.56–7.20(7H, m) | 62.44 (62.70) | 4.86 (4.96) | 7.91 (8.12) |
| 30 | CH₃ | H |  | CH | mp 85–87° C. | 2.17(3H, s) 3.35(2H, s) 5.15(2H, s) 6.60–7.20(7H, m) | 58.13 (58.47) | 3.84 (4.04) | 7.74 (8.02) |

TABLE 1-continued

Structure: Cl-(A ring with R2, R1)-OCH2-C(R3)=N-O-N (isoxazole)

| Compound No. | R1 | R2 | R3 | A | Physical properties | NMR (δ = ppm, CDCl₃) | C Measured (Calculated) | H Measured (Calculated) | N Measured (Calculated) |
|---|---|---|---|---|---|---|---|---|---|
| 31 | Cl | CH₃ | CH₂-C₆H₄-OCH₃ | CH | $n_D^{25}$ 1.5775 | 2.36(3H, s) 3.71(3H, s) 3.95(2H, s) 5.15(2H, s) 6.56–7.25(6H, m) | 56.99 (57.00) | 4.35 (4.25) | 7.72 (7.38) |
| 32 | CH₃ | H | CH₂-C₆H₃(Cl)(Cl) | CH | mp 62.5–64° C. | 2.10(3H, s) 4.10(2H, s) 5.11(2H, s) 6.57–7.25(6H, m) | 53.48 (53.22) | 3.35 (3.41) | 7.01 (7.03) |
| 33 | Cl | H | CH₂-C₆H₃(Cl)(Cl) | CH | mp 82–83.5° C. | 4.16(2H, s) 5.23(2H, s) 6.77–7.33(6H, m) | 47.48 (47.55) | 2.59 (2.49) | 6.84 (6.93) |
| 34 | CH₃ | H | CH₂-C₆H₅ | CH | $n_D^{25}$ 1.5705 | 2.08(3H, s) 3.97(2H, s) 5.05(2H, s) 6.51–7.2(8H, m) | 65.05 (64.86) | 4.91 (4.80) | 8.90 (8.89) |

When the compound of the present invention is used as a herbicide, it may be applied as it is. However, better results can be obtained when it is combined with commonly employed various carriers of diluents, and in some cases, formulated by an addition of an adjuvant into a formulation such as a water soluble powder, an oil solution, a wettable powder, an emulsifiable concentrate, a dust or granules in accordance with a conventional method. These various formulations may be used as they are or may be diluted with water to a prescribed concentration for actual application.

As the agricultural adjuvant, a surfactant, a stabilizer, a binder, an aerosol propellant and a synergistic agent may, for example, be mentioned.

As the diluent, a solvent such as water, an organic solvent, a hydrocarbon, a halogenated hydrocarbon, an alcohol, an ether, an alcohol ether, a ketone, an ester, an amide or a sulfoxide, may be mentioned. As the filler or solid carrier, an inorganic powder such as slaked lime, magnesium lime, gypsum, calcium carbonate, silica, pearlite, pumice, diatomaceous earth, alumina, zeolite, clay minerals (such as talc, vermiculite or kaolinite), a vegetable powder (such as starch, cereals powder or glucose), and a synthetic resin powder (such as a phenol resin, a urea resin or a vinyl chloride resin) may be mentioned.

As the surfactant, an anionic surfactant (such as an alkyl sulfate, an aryl sulfonate, a succinate or a polyethylene glycol alkylaryl ether sulfate), a cationic surfactant (such as an alkylamine or a polyoxyethylene alkylamine), a non-ionic surfactant (such as a polyoxyethylene glycol ether, a polyoxyethylene glycol ester or a polyhydric alcohol ester), and an amphoteric surfactant may be mentioned.

As other adjuvants, a stabilizer, a binder, an effect-prolonging agent, a dispersant and a synergistic agent may be mentioned.

The dose of the compound of the present invention to be used as an active ingredient, may be varied depending upon the type of the formulation, the manner for application, the purpose, the timing and the conditions for the germination of weeds. The dose is usually within a range of from 0.01 to 2 kg/ha, preferably from 0.2 to 1.0 kg/ha.

The compound of the present invention may also be suitably combined with other bactericides, insecticides, miticides, herbicides or plant growth regulating agents to obtain labor-saving herbicides. Particularly when used in combination with other herbicides, it is possible not only to reduce the amount of the active ingredient and save the labor, but also to attain the enlargement of the herbicidal spectrum due to the synergistic effect of the two herbicides or obtain an improved effects due to the synergistic effect.

Such other herbicides include an amide-type herbicide such as 3′,4′-dichloropropionanilide, N,N-dimethyl-2,2-diphenylacetamide or N-[3-(1-ethyl-1-methylpropyl)-5-isooxazol]-2,6-dimethoxybenzamide, an acetylchloride-type herbicide such as N-methoxymethyl-2′,6′-diethyl-2-chloroacetanilide, 2-chloro-2′,6′-diethyl-N-(butoxymethyl)-acetanilide, 2-chloro-2′-ethyl-6′-methyl-N-(2-methoxy-1-methylethyl)acetanilide, ethyl-N-chloroacetyl-N-(2,6-diethylphenyl)amino acetate, N,N-diallyl-2-chloroacetamide or 2-chloro-2′,6′-diethyl-N-(n-propoxyethyl)acetanilide, a dinitroaniline-type herbicide such as 2,6-dinitro-N,N-dipropyl-4-trifluoromethylaniline or 4-(methylsulfonyl)-2,6-dinitro-N,N-dipropylaniline, a thiolcarbamate-type herbicide such as S-(4-chlorobenzyl)-N,N-diethylthiolcarbamate, S-ethyl-N,N-hexamethylene thiolcarbamate, S-(1-methyl-1-phenethyl)piperidine-1-carbathioate, S-benzyl-N-ethyl-N-(1,2-dimethylpropyl)thiolcarbamate or S-isopropyl-hexahydro-1H-azepine-1-carbothioate, a diphenylether type herbicide such as 2,4,6-trichlorophenyl-4-nitrophenyl ether, 2,4-dichlorophenyl-4-nitro-3-methoxyphenyl ether, 2,4-dichlorophenyl-3-methoxycarbonyl-4-nitrophenyl ether, 2-chloro-4-trifluoromethylphenyl-3-ethoxy-4-nitrophenyl ether, sodium-5-[2-chloro-4-(trifluoromethyl)phenoxy]-2-nitrobenzoate, 3-[2-nitro-5-(2-chloro-4-trifluoromethylphenoxy)-phenoxy]tetrahydrofuran, 5-(2'-chloro-4'-trifluoromethylphenoxy)-2-nitro-N-methanesulfonylbenzaimide or methyl-5-(2'-chloro-4'-trifluoromethylphenoxy)-2-nitroacetophenonoxime-o-acetate, and a triazine-type herbicide such as 2-chloro-4,6-bis(ethylamino)-1,3,5-triazine, 2-chloro-4-ethylamino-6-isopropylamino-1,3,5-triazine, 2-methylthiol-4,6-bis(ethylamino)-1,3,5-triazine or 2-methylthio-4,6-bis(isopropylamino)-1,3,5-triazine.

In the herbicidal composition of the present invention, the compound of the formula I is incorporated as the active ingredient usually in an amount of from 0.1 to 90% by weight, preferably from 1 to 80% by weight.

Now, the present invention will be described in further detail with reference to Examples. However, it should be understood that the present invention is by no means restricted to these specific Examples.

EXAMPLE 1

3-(4-Chlorobenzyl)-5-[(2,4-dichlorophenoxy)methyl]-1,2,4-oxadiazole (Compound No. 14)

1.63 g of 2,4-dichlorophenyl, 2.67 g of 3-(4-chlorobenzyl)-5-chloromethyl-1,2,4-oxadiazole and 1.52 g of anhydrous potassium carbonate were added to 50 ml of acetonitrile. The mixture was refluxed under stirring for 16 hours. After cooling the reaction mixture, the inorganic substance was filtered off, and acetonitrile was distilled off. The residue was purified by column chromatography [silica gel, developed with benzene/ethyl acetate=10/1 (v/v)] to obtain 2.08 g (yield: 56.3%) of the desired product. ($n_D^{25}$: 1.5904)

EXAMPLE 2

3-Methyl-5-[3,5-dichloropyridin-2-yl-oxy)methyl]-1,2,4-oxadiazole (Compound No. 5)

1.02 g of 3-methyl-5-hydroxymethyl-1,2,4-oxadiazole and 0.59 g of powdery potassium hydroxide were added to 30 ml of isopropanol, and the mixture was stirred at room temperature for 30 minutes. To this solution, 2.03 g of 2-bromo-3,5-dichloropyridine was added, and the mixture was stirred at room temperature for 18 hours. After the reaction, isopropanol was distilled off, and the residue was purified by column chromatography [silica gel, developed with benzene/ethyl acetate=10/1 (v/v)] to obtain 1.14 g (yield: 49%) of the desired product. ($n_D^{25}$: 1.5484)

EXAMPLE 3

Emulsifiable concentrate

20 Parts ("parts" means "parts by weight", and the same applies hereinafter) of Compound No. 1 of the present invention, 60 parts of xylene and 20 parts of Sorpol 2806B (tradename, manufactured by Toho Kagaku Kogyo K.K.) were uniformly mixed and stirred to obtain an emulsifiable concentrate.

EXAMPLE 4

Wettable powder

20 Parts of Compound No. 11 of the present invention, 10 parts of white carbon, 65 parts of jeeklite and 5 parts of Sorpol 5039 (tradename, manufactured by Toho Kagaku Kogyo K.K.) were mixed and pulverized to obtain a wettable powder.

EXAMPLE 5

Granules

2 Parts of Compound No. 2 of the present invention, 55 parts of bentonite, 40 parts of talc, 2 parts of sodium dodecyl benzene sulfonate and 1 part of dioctyl sulfosuccinate were mixed, and after an addition of a proper amount of water, kneaded. By means of an extrusion granulating machine, the mixture was granulated and dried by a usual method to obtain granules.

EXAMPLE 6

Herbicidal test against paddy field weeds

Paddy field soil was filled in a 1/5000 are Wagner pot, and irrigated. Paddy rice seedlings (variety: Nihonbare) of 2.5 leaf stage were transplanted thereto, and proper amounts of paddy field weeds were also sown. On the 5th day after the transplantation, a predetermined amount of the compound of the present invention was applied in the form of an emulsion.

During the test period, the depth of water in the pot was maintained to be 3 cm. Upon expiration of one month after the treatment with the herbicide, the herbicidal effects against the weeds and the phytotoxicity against paddy rice plants were examined. The results are shown in Table 2. In this table, the case wherein the growth of the crop plants or the weeds are not affected at all by the herbicidal effects of the test compound is represented by "0", and the case wherein the crop plants for the weeds were completely withered is represented by "5", and the evaluation was made on the basis of five ratings in between the two extremities.

TABLE 2

| Compound No. | Does of active ingredient g/a | Herbicidal effects | | | | | | | Phytotoxicity to paddy rice plants |
|---|---|---|---|---|---|---|---|---|---|
| | | Annual weeds | | | | Perenial weeds | | | |
| | | Ela | Rot | Zin | Cyp | Sag | Ali | Sci | |
| 1 | 20 | 5 | 5 | 5 | 5 | 5 | 5 | 4 | 1 |
| | 10 | 4 | 4 | 4 | 4–5 | 3 | 3–4 | 3 | 0 |
| | 5 | 3 | 3 | 3–4 | 3 | 2–3 | 3 | 2 | 0 |
| 2 | 20 | 5 | 5 | 5 | 5 | 5 | 5 | 5 | 1 |
| | 10 | 5 | 5 | 5 | 5 | 5 | 5 | 4 | 0 |
| | 5 | 4 | 4 | 5 | 5 | 4 | 4 | 3 | 0 |
| 3 | 20 | 5 | 5 | 5 | 5 | 5 | 5 | 5 | 1 |
| | 10 | 5 | 5 | 5 | 5 | 5 | 5 | 5 | 0 |
| | 5 | 5 | 5 | 5 | 5 | 5 | 5 | 5 | 0 |

TABLE 2-continued

| Compound No. | Dose of active ingredient g/a | Herbicidal effects | | | | | | | Phytotoxicity to paddy rice plants |
|---|---|---|---|---|---|---|---|---|---|
| | | Annual weeds | | | | Perenial weeds | | | |
| | | Ela | Rot | Zin | Cyp | Sag | Ali | Sci | |
| 4 | 20 | 5 | 5 | 5 | 5 | 4 | 5 | 5 | 1 |
| | 10 | 4 | 4 | 4 | 4 | 4 | 3 | 4–5 | 0 |
| | 5 | 3 | 3 | 3 | 3–4 | 3 | 2 | 4 | 0 |
| 5 | 20 | 5 | 5 | 5 | 5 | 5 | 5 | 5 | 0 |
| | 10 | 5 | 5 | 5 | 5 | 4 | 5 | 5 | 0 |
| | 5 | 5 | 5 | 5 | 5 | 4 | 4–5 | 5 | 0 |
| 6 | 20 | 5 | 5 | 5 | 5 | 5 | 5 | 5 | 0 |
| | 10 | 5 | 5 | 5 | 5 | 5 | 5 | 5 | 0 |
| | 5 | 4 | 4–5 | 3 | 4–5 | 3 | 4 | 4–5 | 0 |
| 8 | 20 | 5 | 5 | 5 | 5 | 4 | 5 | 3 | 0 |
| | 10 | 3 | 3 | 4 | 5 | 3 | 4 | 2 | 0 |
| | 5 | 2 | 2 | 3 | 4 | 2–3 | 4 | 1 | 0 |
| 9 | 20 | 5 | 5 | 5 | 4 | 4 | 3 | 3–4 | 0 |
| | 10 | 5 | 5 | 5 | 3 | 3 | 2 | 3 | 0 |
| | 5 | 3 | 3 | 4 | 2 | 2 | 1 | 2 | 0 |
| 10 | 20 | 5 | 5 | 5 | 5 | 5 | 5 | 5 | 1 |
| | 10 | 5 | 5 | 5 | 5 | 5 | 5 | 5 | 0 |
| | 5 | 5 | 5 | 5 | 5 | 5 | 4–5 | 4 | 0 |
| 11 | 20 | 5 | 5 | 5 | 5 | 5 | 5 | 5 | 0 |
| | 10 | 5 | 5 | 5 | 5 | 4 | 4 | 5 | 0 |
| | 5 | 4 | 4 | 3–4 | 4 | 3–4 | 3 | 4–5 | 0 |
| 12 | 20 | 5 | 5 | 5 | 5 | 5 | 5 | 5 | 0 |
| | 10 | 4 | 4 | 5 | 4 | 4 | 4 | 4 | 0 |
| | 5 | 3 | 3 | 4 | 4 | 3 | 3–4 | 3 | 0 |
| 13 | 20 | 5 | 5 | 5 | 5 | 4 | 4 | 5 | 0 |
| | 10 | 4 | 4 | 3–4 | 4 | 3 | 3 | 4 | 0 |
| | 5 | 3 | 3 | 3 | 2 | 2 | 2 | 3 | 0 |
| 14 | 20 | 5 | 5 | 5 | 5 | 5 | 5 | 5 | 1 |
| | 10 | 5 | 5 | 5 | 5 | 5 | 5 | 5 | 0 |
| | 5 | 5 | 5 | 5 | 5 | 5 | 4–5 | 4–5 | 0 |
| 17 | 20 | 5 | 5 | 5 | 5 | 5 | 5 | 5 | 0 |
| | 10 | 5 | 5 | 5 | 5 | 5 | 5 | 5 | 0 |
| | 5 | 5 | 5 | 4 | 4 | 4 | 5 | 4 | 0 |
| 20 | 20 | 5 | 5 | 5 | 5 | 5 | 5 | 3 | 0 |
| | 10 | 4 | 4 | 4 | 5 | 3 | 3 | 2 | 0 |
| | 5 | 3 | 3 | 3–4 | 2 | 2 | 2 | 1 | 0 |
| 23 | 20 | 5 | 5 | 5 | 5 | 5 | 5 | 5 | 0 |
| | 10 | 5 | 4–5 | 4 | 5 | 4–5 | 5 | 5 | 0 |
| | 5 | 4 | 4 | 4 | 5 | 4 | 4 | 4 | 0 |
| 26 | 20 | 5 | 5 | 5 | 5 | 5 | 5 | 5 | 0 |
| | 10 | 5 | 5 | 5 | 5 | 5 | 5 | 5 | 0 |
| | 5 | 5 | 5 | 5 | 5 | 5 | 4–5 | 4–5 | 0 |
| 29 | 20 | 5 | 5 | 5 | 5 | 5 | 5 | 5 | 0 |
| | 10 | 5 | 5 | 5 | 5 | 4 | 4 | 4 | 0 |
| | 5 | 5 | 4–5 | 4 | 5 | 3–4 | 3 | 3–4 | 0 |
| 30 | 20 | 5 | 5 | 5 | 5 | 5 | 5 | 5 | 0 |
| | 10 | 5 | 5 | 5 | 5 | 4 | 4 | 4 | 0 |
| | 5 | 4 | 4 | 3 | 3 | 3 | 3 | 2 | 0 |
| 31 | 20 | 5 | 5 | 5 | 5 | 5 | 5 | 5 | 0 |
| | 10 | 5 | 5 | 5 | 5 | 4–5 | 4–5 | 4–5 | 0 |
| | 5 | 5 | 5 | 4–5 | 4 | 4 | 4 | 4 | 0 |
| 32 | 20 | 5 | 5 | 5 | 5 | 5 | 5 | 5 | 0 |
| | 10 | 5 | 5 | 5 | 5 | 4 | 4 | 4 | 0 |
| | 5 | 4 | 4 | 3–4 | 4 | 3 | 3 | 3–4 | 0 |
| 33 | 20 | 5 | 5 | 5 | 5 | 5 | 5 | 5 | 0 |
| | 10 | 5 | 5 | 4 | 4 | 4 | 4 | 3 | 0 |
| | 5 | 4–5 | 3 | 3 | 4 | 3 | 3 | 2–3 | 0 |
| 34 | 20 | 5 | 5 | 5 | 5 | 5 | 5 | 5 | 0 |
| | 10 | 5 | 5 | 5 | 5 | 5 | 5 | 5 | 0 |
| | 5 | 5 | 5 | 5 | 5 | 4 | 4 | 5 | 0 |
| Control compound MCP (NA)* | 20 | 5 | 5 | 5 | 5 | 5 | 5 | 5 | 3–4 |
| | 10 | 5 | 5 | 5 | 5 | 4 | 4 | 3 | 3 |
| | 5 | 3 | 4 | 4 | 4 | 3 | 2 | 2 | 2 |

*Sodium 2-methyl-4-chlorophenoxy acetate
Ela: american water wort (*Elatine triandra*)
Rot: tooth cup (*Rotala indica*)
Zin: false pimpunel (*Lindernia procumben's*)
Cyp: flat-sedge (*Cyperus microiria*)
Sag: arrowhead (*Sagittaria pyamaea*)
Ali: narrow-leaved arrowhead (*Alisma canaliculatum*)
Sci: bulrush (*Scirpus hotarui*)

EXAMPLE 7

Herbicidal test against upland weeds

Diluvium soil was filled in an unglazed pot having a diameter of 20 cm. Seeds of weeds and seeds of rice, corn and wheat were sown thereto, and covered with soil. The pot was kept in a greenhouse. When the weeds and crop plants reached a level of 3–4 leaf stage, a test compound was formulated into an emulsifiable concentrate, and a predetermined amount thereof was diluted with water and sprayed over the leaves and stems of the plants by means of a small size spraying machine. The herbicidal effects against the weeds and the phytotoxicity against the crop plants were examined upon expiration of one month from the application. The results are shown in Table 3. The evaluation standards for the herbicidal effects and for the phytotoxicity were the same as in Example 6.

TABLE 3

| Compound No. | Dose of active ingredient g/a | Herbicidal effects | | | | Phytotoxicity to crop plants | | |
|---|---|---|---|---|---|---|---|---|
| | | Che | Pol | Ste | Ama | Ory | Zea | Tri |
| 1 | 10 | 4 | 4-5 | 4-5 | 4 | 0 | 0 | 0 |
|  | 20 | 5 | 5 | 5 | 5 | 1 | 0 | 1 |
| 2 | 10 | 5 | 5 | 4-5 | 4-5 | 0 | 0 | 0 |
|  | 20 | 5 | 5 | 5 | 5 | 1 | 0 | 1 |
| 3 | 10 | 5 | 5 | 5 | 5 | 0 | 0 | 0 |
|  | 20 | 5 | 5 | 5 | 5 | 0 | 0 | 0 |
| 4 | 10 | 4 | 4 | 4 | 4 | 0 | 0 | 0 |
|  | 20 | 5 | 5 | 5 | 5 | 1 | 0 | 1 |
| 5 | 10 | 4 | 4 | 4 | 4 | 0 | 0 | 0 |
|  | 20 | 5 | 5 | 5 | 5 | 0 | 0 | 0 |
| 6 | 10 | 5 | 5 | 4-5 | 5 | 0 | 0 | 0 |
|  | 20 | 5 | 5 | 5 | 5 | 1 | 0 | 1 |
| 7 | 10 | 5 | 5 | 3-4 | 4 | 0 | 0 | 0 |
|  | 20 | 5 | 5 | 5 | 5 | 1 | 0 | 1 |
| 8 | 10 | 4 | 4-5 | 4-5 | 4-5 | 0 | 0 | 0 |
|  | 20 | 5 | 5 | 5 | 5 | 1 | 0 | 1 |
| 9 | 10 | 4 | 4 | 4 | 4-5 | 0 | 0 | 0 |
|  | 20 | 5 | 5 | 5 | 5 | 0 | 0 | 0 |
| 10 | 10 | 5 | 5 | 4-5 | 4-5 | 0 | 0 | 0 |
|  | 20 | 5 | 5 | 5 | 5 | 1 | 0 | 1 |
| 11 | 10 | 5 | 4 | 4 | 3 | 0 | 0 | 0 |
|  | 20 | 5 | 5 | 5 | 5 | 0 | 0 | 0 |
| 12 | 10 | 5 | 4 | 4 | 4 | 0 | 0 | 0 |
|  | 20 | 5 | 5 | 5 | 5 | 0 | 0 | 0 |
| 13 | 10 | 5 | 5 | 4-5 | 4 | 0 | 0 | 0 |
|  | 20 | 5 | 5 | 5 | 5 | 0 | 0 | 0 |
| 14 | 10 | 5 | 5 | 5 | 5 | 0 | 0 | 0 |
|  | 20 | 5 | 5 | 5 | 5 | 1 | 0 | 1 |
| 15 | 10 | 4-5 | 4-5 | 4 | 4 | 0 | 0 | 0 |
|  | 20 | 5 | 5 | 5 | 5 | 1 | 0 | 1 |
| 17 | 10 | 5 | 5 | 5 | 4-5 | 0 | 0 | 0 |
|  | 20 | 5 | 5 | 5 | 5 | 1 | 0 | 1 |
| 19 | 10 | 4 | 4 | 4 | 4 | 0 | 0 | 0 |
|  | 20 | 5 | 5 | 5 | 5 | 0 | 0 | 0 |
| 20 | 10 | 3-4 | 3-4 | 4 | 3 | 0 | 0 | 0 |
|  | 20 | 5 | 5 | 5 | 5 | 0 | 0 | 0 |
| 21 | 10 | 4 | 4-5 | 4 | 4-5 | 0 | 0 | 0 |
|  | 20 | 5 | 5 | 5 | 5 | 0 | 0 | 0 |
| 22 | 10 | 4 | 4 | 3 | 3 | 0 | 0 | 0 |
|  | 20 | 5 | 5 | 5 | 5 | 0 | 0 | 0 |
| 23 | 10 | 5 | 5 | 4-5 | 4-5 | 0 | 0 | 0 |
|  | 20 | 5 | 5 | 5 | 5 | 0 | 0 | 0 |
| 25 | 10 | 4 | 4 | 4 | 4-5 | 0 | 0 | 0 |
|  | 20 | 5 | 5 | 5 | 5 | 0 | 0 | 0 |
| 26 | 10 | 5 | 4 | 4 | 4 | 0 | 0 | 0 |
|  | 20 | 5 | 5 | 5 | 5 | 0 | 0 | 0 |
| 27 | 10 | 5 | 5 | 4-5 | 4-5 | 0 | 0 | 0 |
|  | 20 | 5 | 5 | 5 | 5 | 0 | 0 | 0 |
| 29 | 10 | 3 | 3 | 3 | 3 | 0 | 0 | 0 |
|  | 20 | 5 | 5 | 5 | 5 | 0 | 0 | 0 |
| 30 | 10 | 4 | 4 | 4-5 | 4 | 0 | 0 | 0 |
|  | 20 | 5 | 5 | 5 | 5 | 0 | 0 | 0 |
| 31 | 10 | 5 | 5 | 5 | 5 | 0 | 0 | 0 |
|  | 20 | 5 | 5 | 5 | 5 | 0 | 0 | 0 |
| 32 | 10 | 4 | 4 | 4-5 | 4 | 0 | 0 | 0 |
|  | 20 | 5 | 5 | 5 | 5 | 0 | 0 | 0 |
| 33 | 10 | 3-4 | 4 | 4 | 4-5 | 0 | 0 | 0 |
|  | 20 | 5 | 5 | 5 | 5 | 0 | 0 | 0 |
| 34 | 10 | 5 | 5 | 5 | 5 | 0 | 0 | 0 |
|  | 20 | 5 | 5 | 5 | 5 | 0 | 0 | 0 |
| Compound MCP (Na)* | 10 | 4 | 4 | 5 | 5 | 3 | 2 | 3 |
|  | 20 | 5 | 5 | 5 | 5 | 4 | 3 | 4 |

*Sodium 2-methyl-4-chlorophenoxy acetate
Che: lambsquarter (*Chenopodium album*)
Pol: smartweed (*Polygonum hydropiper*)
Ste: common chickweed (*Stellaria media*)
Ama: slender amarauth (*Amaranthus viridis*)
Ory: rice (*Oryza sativa*)
Zea: corn (*Zea mays*)
Tri: wheat (*Triticum*)

The herbicide containing the compound of the present invention as an active ingredient is a herbicide which can be used extremely safely for either soil treatment or foliage treatment for gramineous crop plants such as rice, corn, sugar cane, wheat, barley, rye or lawn grass and which is capable of certainly controlling annual and perennial broad leaf weeds and cyperaceous weeds.

What is claimed is:

1. A 1,2,4-oxadiazole derivative having the formula:

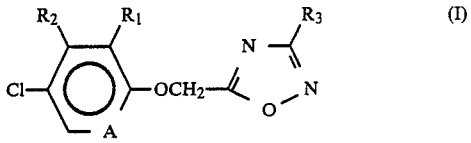

wherein A is a methine group or a nitrogen atom; $R_1$ is a chlorine atom or a methyl group; when A is a methine group and $R_1$ is a methyl group, $R_2$ is a hydrogen atom; when A is a methine group and $R_1$ is a chlorine atom, $R_2$ is a hydrogen atom or a methyl group; and when A is a nitrogen atom, $R_2$ is a hydrogen atom; $R_3$ is a hydrogen atom, an alkyl group having from 1 to 11 carbon atoms, a benzyl group unsubstituted or substituted by chlorine or methoxy; a phenoxymethyl group unsubstituted or substituted by chlorine or methyl, or a lower alkoxyalkyl group.

2. The compound of the formula I according to claim 1, wherein A is a methine group; $R_1$ is a chlorine atom, $R_2$ is a hydrogen atom or a methyl group; and $R_3$ is a hydrogen atom, a methyl group, an ethyl group, a pentyl group, an octyl group, a methoxymethyl group, a methoxyethyl group, an ethoxyethyl group, an undecyl group, a benzyl group unsubstituted or substituted by chlorine or methoxy, a phenoxymethyl group unsubstituted or substituted by chlorine or methyl.

3. The compound of the formula I according to claim 1, wherein A is a nitrogen atom, $R_1$ is a chlorine atom, $R_2$ is a hydrogen atom, and $R_3$ is an ethyl group, a benzyl group unsubstituted or substituted by chlorine, an unsubstituted phenoxymethyl group.

4. A selective herbicidal composition comprising a herbicidally effective amount of a 1,2,4-oxadiazole derivative of the formula I as defined in claim 1, and an agricultural adjuvant.

5. A method for killing weeds, which comprises applying a herbicially effective amount of a 1,2,4-oxadiazole derivative of the formula I as defined in claim 1 to a locus to be protected.

* * * * *